United States Patent [19]
James

[11] Patent Number: 5,558,090
[45] Date of Patent: Sep. 24, 1996

[54] MULTI-PURPOSE HEAD-MOUNTED ADJUSTABLE MEDICAL TUBE HOLDER

[76] Inventor: Lonnie A. James, 63 E. 2nd St., Huntington Station, N.Y. 11746

[21] Appl. No.: 549,872

[22] Filed: Oct. 30, 1995

[51] Int. Cl.⁶ .......................... A61M 25/02; A61M 16/04
[52] U.S. Cl. ................. 128/207.18; 128/207.17; 128/DIG. 26
[58] Field of Search ........... 128/200.26, 207.14, 128/207.15, 207.17, 207.18, 207.13, DIG. 26; 604/94, 179, 180

[56] References Cited

U.S. PATENT DOCUMENTS

| | | | |
|---|---|---|---|
| 4,018,221 | 4/1977 | Rennie | 128/207.18 |
| 4,502,478 | 3/1985 | Lifton | 128/207.14 |
| 4,665,566 | 5/1987 | Garrow | 128/207.18 X |
| 4,744,358 | 5/1988 | McGinnis | 128/207.17 |
| 4,774,946 | 10/1988 | Ackerman et al. | 128/207.18 |
| 4,808,160 | 2/1989 | Timmons et al. | 604/94 |
| 5,009,227 | 4/1991 | Nieuwstad | 128/207.17 |
| 5,402,776 | 4/1995 | Islava | 128/207.17 |
| 5,419,319 | 5/1995 | Werner | 128/207.17 |
| 5,437,273 | 8/1995 | Bates et al. | 128/207.17 |

*Primary Examiner*—Edgar S. Burr
*Assistant Examiner*—Eric P. Raciti
*Attorney, Agent, or Firm*—Michael I. Kroll

[57] ABSTRACT

A multi-purpose adjustable tube holder is provided, which consists of an endotracheal tube holder including an endotracheal tube securing device having a clamp for clamping an endotracheal tube into a tube channel wherein the tube holder is supported in front of the patient's mouth by the brow band secured to the patient by a head band on the head of the patient.

10 Claims, 2 Drawing Sheets

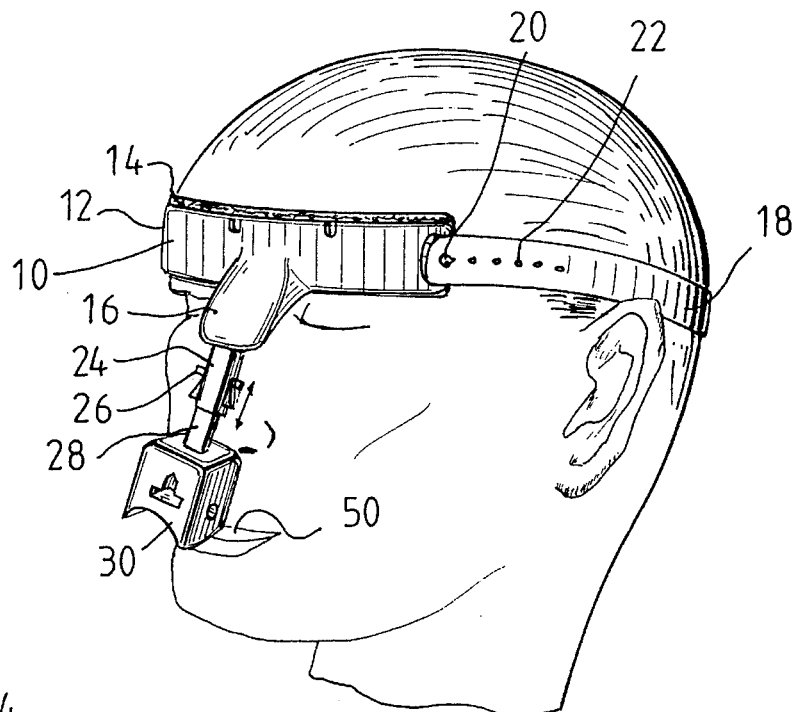
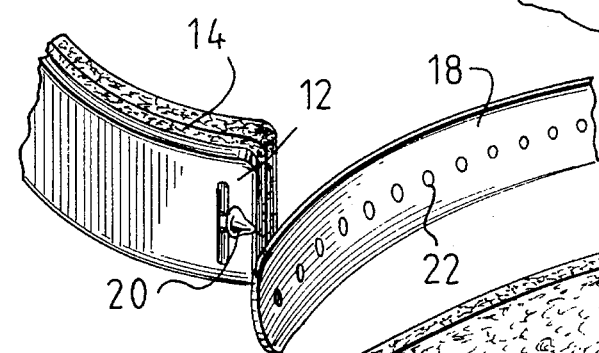
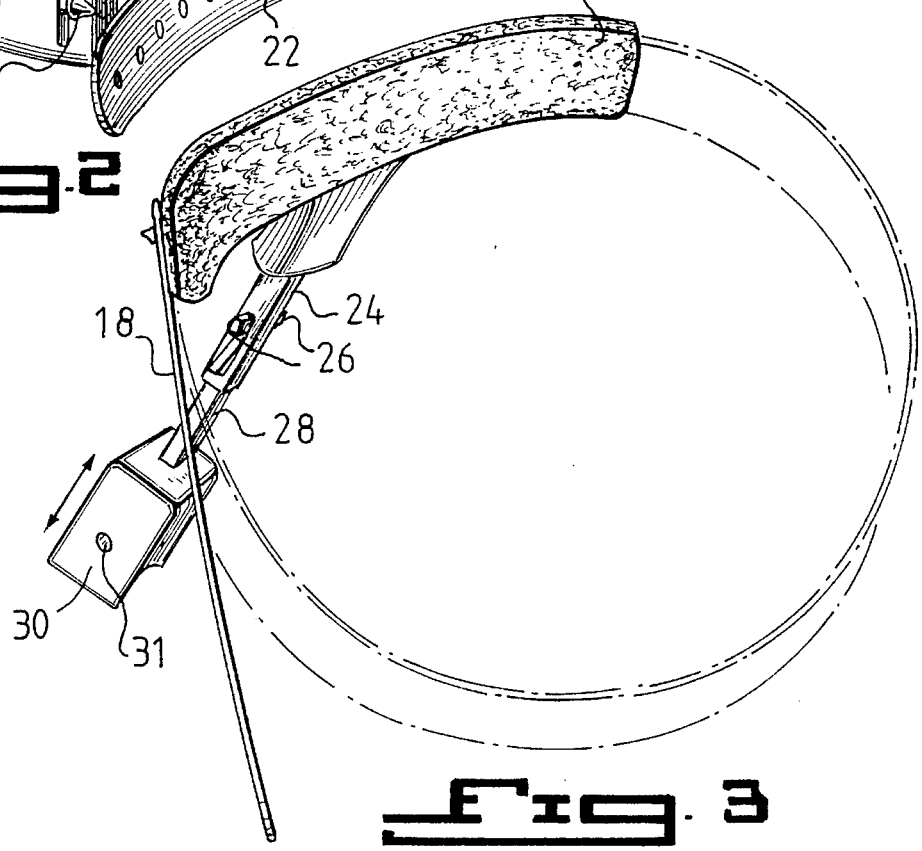

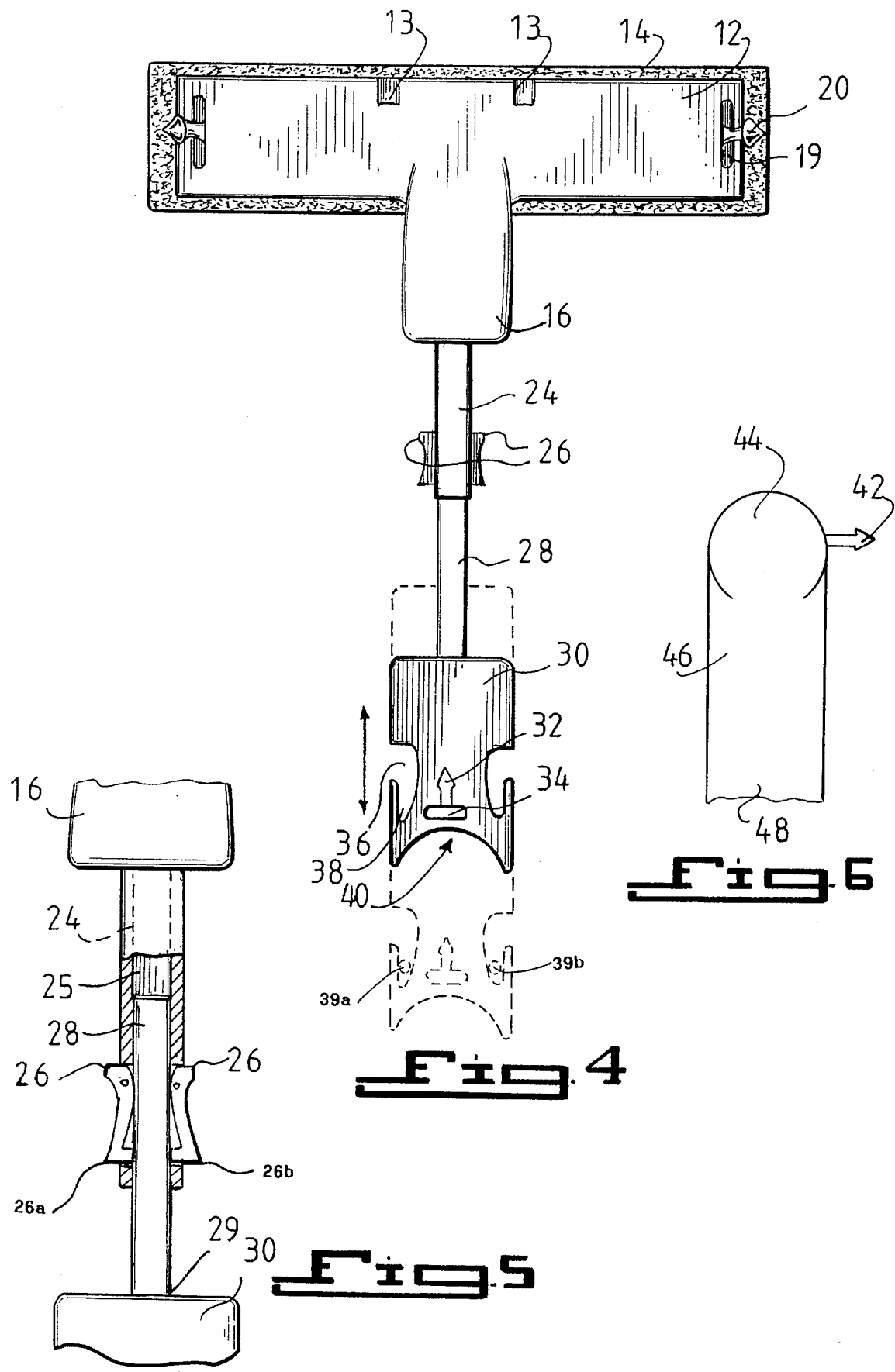

MULTI-PURPOSE HEAD-MOUNTED ADJUSTABLE MEDICAL TUBE HOLDER

BACKGROUND OF THE INVENTION

1. Field of the Invention

The instant invention relates generally to an endotracheal apparatus and more specifically it relates to an endotracheal tube holding and securing apparatus.

2. Background of the Invention

Frequently, convalescing patients require continuous medical treatment such as that provided by medical devices assisting with respiration, medication, monitoring and/or drainage of bodily fluids of the patient. These medical devices typically require lengths of medical tubing, such as catheters, ventilators, electrical leads and the like, attached between the patient and a base unit to provide treatment. Because the medical tubing must be maintained in a relatively fixed position on the patient for extended periods of time, it is desirable to attach the tubing to the patient to accommodate movement of the patient without disturbing the attachment of the tubing.

Often times, for lack of a fully versatile band, the medical tubing is attached by taping the tubing down against the patient's skin or clothing. Clearly, tape is the least desirable choice for securing and aligning medial tubing relative a patient, since patient excretions such as perspiration, blood or saliva can wet the tape, causing it to loosen and the medical tubing to become dislodged. As a result, there are presently a number of devices available for securing catheters and the like to a person's limb.

A need therefore exists for an improved multi-purpose adjustable tube holder which both secures and aligns a tubular medical device adjacent a portion of a human body. Such a multi-purpose adjustable tube holder should be tape-free to avoid the many problems associated with taping tubular medical devices to a patient's skin or clothing while still providing the attachment versatility of tape. Also, such a device should securely affix the medical tubing, and to prevent irritation and gouging caused by movement of the medical tubing relative the patient and provide cushioning between the tubing and the patient. Therefore, the device should be without metallic mechanical attachments, such as metal hooks and buttons.

Further, such a device should be conveniently and efficiently manipulated to secure and align medical tubing relative the patient, without requiring disconnection of the medical tubing for use with the device and without semi-permanently attaching the device to the medical tubing. Preferably, such a device should be infinitely adjustable both with respect to the secure mounting of the tubular medical device to the multi-purpose adjustable tube holder. Most importantly, such a device should permit the adjustment of the location of the tubing relative to the patient's mouth without a re-positioning or otherwise affecting the multi-purpose adjustable tube holder. Ideally, such a device should be simple to manufacture so that it may be economical and sterilizable or sanitarily discarded after use.

This invention is also designed for comfort, and to stabilize the endotracheal tube, nasal tracheal tube, stomach pump and tube feeding tubes after they are secured. In addition, the present invention prevents numbness, necrosis of the lips, bacteria build up, halitosis, sores and thereby improves the quality of patient treatment. The endotracheal tube and nasal tracheal tube are used to administer oxygen to the rings by means of mechanical ventilators of T-pieces.

The feeding tube is for food injestion and the stomach pump tube is for removing the contents of the stomach. The bite block is used to prevent the patient from biting the endotracheal tube and cutting off the supply of oxygen to the lungs.

Numerous endotracheal devices have been provided in prior art. While these units may be suitable for the particular purpose to which they address, they would not be as suitable for the purposes of the present invention as heretofore described.

SUMMARY OF THE INVENTION

Endotracheal and nasotracheal tubes are cannulae used to maintain an open air passage for breathing under various circumstances. They are commonly used for the introduction of air and anesthetic during surgery, and are frequently used for considerable periods following surgery. They are also used in cases in which mechanical ventilation is required.

The object of the present invention is to provide a holder which overcomes the various disadvantages of adhesive tape, and which is superior to other proposed cannula holders in the following respects individually and in combination. The cannula holder in accordance with the invention holds the cannula or tube securely in position while allowing for oral care. The multi-purpose adjustable tube holder accommodates various different sizes of tubes as well as various different kinds of tubes, including both endotracheal and nasotracheal tubes. The holder in accordance with the invention is extremely simple in structure, adjustable and easy to use, comfortable to the patient, and neat in appearance. Unlike tape, it does no require frequent replacement. Furthermore, it may be affixed to the patient in a simple head band device in order to accommodate different situations.

The present invention contemplates an endotracheal tube holding and securing apparatus which alleviates the above and other problems. The present invention contemplates in one aspect thereof an endotracheal tube holder which includes a head band which provides for improved ease of patient oral care and related nursing care, as well as improved patient comfort. The multi-purpose adjustable tube holder of the present invention also contemplates an improved head band system which not only secures the tube holder in front of the patient's face with a minimum of patient discomfort, but in addition provides means for guiding the external run of nasal tubes when such are to be used.

A primary object of the present invention is to provide an endotracheal tube holder that will overcome the shortcomings of the prior art devices.

One object of the present invention is to provide an improved endotracheal tube holding device incorporating a head band which both secures and aligns medical tubing to a patient's mouth.

Another object of the present invention is to provide an endotracheal tube holder incorporating a head band which is adhesive-free to avoid the many problems associated with taping medical tubing to a patient's skin or clothing, while still providing the attachment versatility of tape.

Yet another object of the present invention is to provide an endotracheal tube holder incorporating a head band which securely affixes medical tubing relative a patient's mouth to discourage self or accidental removal and disconnection of the medical tubing, and to prevent irritation and gouging caused by movement of the medical tubing relative the patient.

Still yet another object of the present invention is to provide an endotracheal tube holder incorporating a head band which is comfortable to the patient and provides cushioning between the head band and spacing between the tubing and the patient's mouth.

Yet still another object of the present invention is to provide an endotracheal tube holder which is comfortable to the patient and provides a bite block to position the tubing within the patient's mouth and prevent collapse of the tubing due to biting.

Still another object of the present invention is to provide an endotracheal tube holder void of metallic mechanical attachments, such as metal hooks and buttons.

Yet another object of the present invention is to provide an endotracheal tube holder band which is conveniently and efficiently manipulated to secure and align medical tubing relative the patient's mouth.

Still yet another object of the present invention is to provide an endotracheal tube holder which is infinitely adjustable both with respect to the secure mounting of the head band to the patient's head and the secure mounting of the tubular medical device to the head band in relation to the patient's mouth.

Still another object of the present invention is to provide an endotracheal tube holder which permits the adjustment of the location of the tubing relative the head band without re-positioning or otherwise affecting the head band.

Still yet another object of the present invention is to provide an endotracheal tube holder which resists accidental lavaging of accumulated moisture and degradation and is simple to manufacture so that it may be economically sterilized or sanitarily discarded after use.

Yet another object of the present invention is to provide an endotracheal tube holder which is secured to a patient's head in a manner to minimize shifting, bending and other movement of the tube in the patient's airway without resorting to adhesive tape, elastic bands, or other prior constraints.

Still another object of the present invention is to provide an endotracheal tube holder which offers access to the patient's mouth or normally required oral care and other nursing care without removal of the tube or tube holder.

A further object is to provide an endotracheal holder that is simple and easy to use.

A still further object is to provide an endotracheal holder that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of a multi-purpose adjustable tube holder (MPATH) positioned on the head of a patient;

FIG. 2 is a perspective view of an adjustable head band and brow band connecting means;

FIG. 3 is a perspective view of a multi-purpose adjustable tube holder (MPATH) exhibiting an adjustable head band connected to a brow band with the adjustable tube holder extending downward from the brow band;

FIG. 4 is a front view of a multi-purpose adjustable tube holder (MPATH) exhibiting the tube holder extending upward and downward by adjusting means;

FIG. 5 is a cross-sectional front view of an adjustable tube holder sleeve; and

FIG. 6 is a top view of a bite block.

DETAILED DESCRIPTION OF THE PREFERRED EMBODIMENTS

Turning now descriptively to the drawings, in which similar reference characters denote similar elements throughout the several views, FIGS. 1 through 6 illustrate a multi-purpose adjustable tube holder (MPATH) 10, which consists of a brow band 12 which is connected to a brow band cushion 13 by brow band cushion connectors 14. The brow band 12 is held in place by an adjustable head band 18 by means of a head band adjustment peg 20 located within a headband adjustment peg slot 19 which inserts into a head band adjustment hole 22.

An upper tube holder adjustable sleeve 24 is connected to an adjustable clip 26 that is interspersed above the lower tube holder adjustable sleeve 28 which is inserted into the inner part 25 of the upper tube holder adjustment sleeve. When the tops of clips 26 are squeezed, the bottom ends 26a and 26b are separated thereby permitting lower sleeve 28 to be adjusted within upper sleeve 24. Clip 26 would incorporate a biasing spring (not shown) as is understood in the art.

Medical personnel may readily position adjustable clip 26 to properly secure or clamp sleeve 28 into position for a particular patient, depending upon the dimensions of a patient's head. A screw incorporated into adjustable clip 26 may, for example, be loosened or tightened for the purpose of positioning clip 26 to properly secure or clamp the adjustable tube 28.

The lower tube holder adjustable sleeve 28 is rigidly connected to the tube holder 30 by means of a tube holder adjustable sleeve peg 31 and lower tube holder adjustable sleeve 29.

The bite block 48 is attached to the tube holder 30 by means of a bite block attachment peg 42. The latter would fit into peg receptor slot 34 and be pushed into the bit block peg receptor adjoining slot. The details of the manner by which bit block 48 is connected to holder 30 are conventional and do not form a part of this invention. Holder 30 is shown somewhat schematically in the figures so as not to obscure the principles of the invention.

The lower bite block 46 is inserted into the patient's mouth 50.

The endotracheal tubes are attached in position on the tube holder 30 by means of a tube receptor slot 36 and tube clamp 38 in which endotracheal tubes 39a and 39b are shown in phantom.

The tube holder 30 has a tube holder concave indent 40 to facilitate entry of materials, medications and additional apparatus into the patient's mouth 50.

Adjustable tube holder 10 is manufactured from material capable of withstanding the sterilization process of autoclaving, a low cost material which can be cost effectively discarded after use, and light weight plastic material.

LIST OF REFERENCE NUMERALS 10 multi-purpose adjustable tube holder (MPATH)
12 brow band 13 brow band cushion
14 brow band cushion connectors
16 brow band extension
18 adjustable head band
19 head band adjustment peg slot
20 head band adjustment peg
22 head band adjustment holes
24 upper tube holder adjustable sleeve
26 adjustable knob
26a bottom ends of clip
26b bottom ends of clip
28 lower tube holder adjustable sleeve
29 lower tube holder adjustable sleeve receptor
30 tube holder
31 tube holder adjustable sleeve peg
32 bite block peg receptor
34 bite block peg receptor slot
36 tube receptor slot
38 tube clamp
39a endotracheal tube
39b endotracheal tube
40 tube holder concave indent
42 bite block attachment peg
44 upper bite block
46 lower bite block
48 bite block
50 patient's mouth It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letter Patent is set forth in the appended claims:

1. An endotracheal holder apparatus for securing an endotracheal tube in the operative position thereof in the airway of a patient, comprising:

a) a head band including an adjustable strap connected directly to a brow band having a brow band extension projecting outwardly;

b) an adjustable rigid support sleeve downwardly extending from said brow band extension capable of positioning an endotracheal tube in the proper position within a patient's airway; and c) tube holding means affixed to the bottom of said support sleeve to facilitate positioning of an endotracheal tube and prevent collapse due to patient's biting of endotracheal tube, said tube holding means having slot means for receiving and holding an endotracheal tube entering the mouth of a patient and means for permitting a bite block to be attached, said tube holding means being shaped to facilitate entry of material, medication and additional apparatus into the mouth of a patient while an endotracheal tube is in place.

2. An endotracheal tube holder apparatus as described in claim 1, whereas said brow band contains a cushioning means for the comfort of a patient while using said apparatus.

3. An endotracheal tube holder apparatus as described in claim 2, whereas said head band is transversely flexible with respect to adjacent portions of the brow band.

4. An endotracheal tube holder apparatus as described in claim 1, whereas said head band comprises an elongated non-extensible head band adapted to generally horizontally encompass the head of such a patient and a non-extensible adjustable overhead strap affixed to said head band adapted to extend over the head of such a patient from side to side.

5. An endotracheal tube holder apparatus as described in claim 1, whereas said tube holder means is indented in a concave fashion to accommodate additional medical treatments or devices entering a patient's mouth.

6. An endotracheal tube holder apparatus as described in claim 1, whereas said adjustable sleeve comprises a lower sleeve slidably received within an upper sleeve and having side member means which when squeezed permits rapid adjustment of the length of said sleeve means.

7. An endotracheal tube holder apparatus as described in claim 1, whereas said endotracheal tube holder apparatus is manufactured from material capable of withstanding the sterilization process of autoclaving.

8. An endotracheal tube holder apparatus as described in claim 1, whereas said endotracheal tube holder apparatus is manufactured from a low cost material which can be cost effectively discarded after use.

9. An endotracheal tube holder apparatus as described in claim 1, whereas said endotracheal tube holder apparatus is manufactured from light weight plastic material.

10. An endotracheal tube holder apparatus as described in claim 1, whereas said head band is manufactured from an elastic material.

* * * * *